May 12, 1959 J. J. FLAD Plant Pat. 1,832
GLADIOLUS PLANT
Filed Feb. 27, 1958
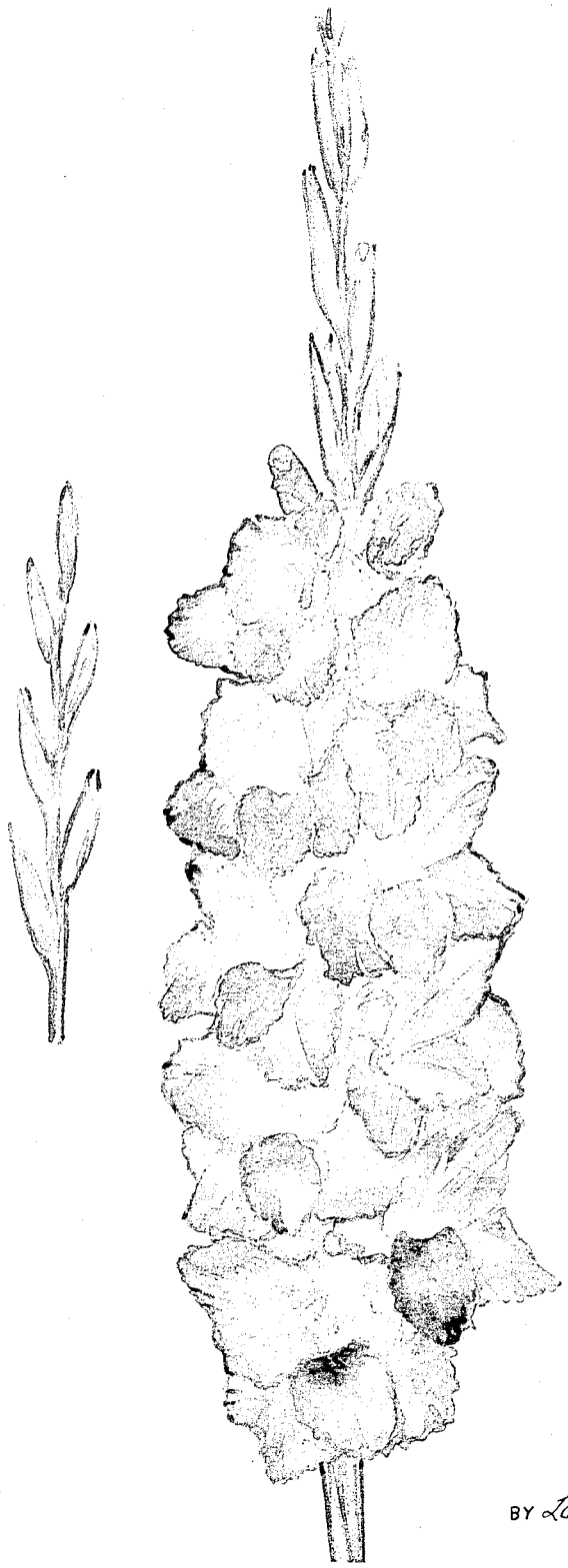
INVENTOR
JOHN J. FLAD
BY Lamont Johnston
ATTORNEY United States Patent Office Plant Pat. 1,832
Patented May 12, 1959

1,832

GLADIOLUS PLANT

John J. Flad, Madison, Wis., assignor to Selected Glads, Inc., Nashville, Tenn., a corporation of Tennessee Application February 27, 1958, Serial No. 718,101

1 Claim. (Cl. 47—60)

My present invention relates to a new and improved variety of gladiolus and is notable particularly for its unusual color, health and precocity.

My new gladiolus in the result of a cross between Traveler (unpatented), the seed parent, and Edgewood (unpatented), the pollen parent. This cross was made by me in my garden at Madison, Wisconsin, by hand pollination. This new variety has been asexually reproduced in my garden at Madison, Wisconsin, by natural increase from cormels through several generations and its characteristics seem to be permanently fixed.

The illustration accompanying this specification shows two views of a single bloom spike of this variety in approximately the true color, but generally reduced in size. The view to the right shows the lower part of the spike and the view to the left shows the upper part.

In the following detailed description, the color plate references are to the "Horticultural Color Chart" by The British Colour Council. Where there are other references to color, the ordinary dictionary means of the terms are intended.

The following is a more complete description of the plant and flower of this new variety.

*The plant*

Growth: Very vigoous; exceedingly robust. Plant grows to a height of 60" under normal conditions.

Blooming: Each spike generally has a total of 18 to 20 buds and flowers with 6 to 8 being open at once.

Resistance to disease: This new variety has been grown in various soils in Dane County, Wisconsin, under the natural conditions provided by the climate of the area. It has been under observation both in separate plots and among other varieties of gladiolus plants. At the end of the season, other varieties in the same plots had been badly affected by various diseases, including Botrytis and Sclerotinia dry rot, whereas I found that this variety remained extremely healthy and unaffected by diseases.

Foliage: Dark green; 6 to 8 leaves. Upright. Leaves up to 30" high and about 3 inches wide.

Stems: Stiff and strong and perfectly straight. Diameter at base is about ⅝".

Spike: Length of flower head is about 27 inches on an average.

Corms: This variety has a very dark bulb. The flesh is Oxblood Red (00823). The husks have a reddish cast.

*The flower*

Spike: Long slender; has 18–20 buds and opens 3 to 4 the first day, followed by 7 to 9 open the second day.

Arrangement: The florets are gracefully arranged in a somewhat double-row fashion and almost always all the florets face the same direction.

Buds: 5 to 6 buds will show color at once. Opening buds are about 2½" long.

Size: Individual florets measure about 5 inches without distortion.

Form: Florets are wide open, gently recurved and round.

Petals: Show a slight fluting and are somewhat ruffled and are heavy substanced.

Color: Rose Red (724) comes closest to the true color.

Reproductive organs:

*Stamens.*—Dark Dull Violet (36).

*Pistils.*—Nearly white; extend about same distance as stamens.

*Comparisons*

My new variety resembles Edgewood, unpatented, more than any other variety but differs from it principally as follows:

(1) My variety is a much finer color than Edgewood. Edgewood fades to a lighter color in the upper part of the floret and my variety is nearly the same color throughout.

(2) My variety produces better, heavier, higher crowned bulbs than Edgewood.

(3) My variety is more prolific than Edgewood.

(4) My variety has heavier substance and florets are more gracefully arranged on the stem than Edgewood.

Having thus disclosed my invention, I claim:

The new variety of gladiolus plant substantially as herein described and illustrated, characterized by its unusual color, superior health and propagation, and heavier substance.

No references cited.